(12) United States Patent
Mclaughlin et al.

(10) Patent No.: US 12,429,141 B2
(45) Date of Patent: *Sep. 30, 2025

(54) LOW FORCE VALVES FOR DRUG DELIVERY PUMPS

(71) Applicant: INSULET CORPORATION, Acton, MA (US)

(72) Inventors: Ian Mclaughlin, Groton, MA (US); Daniel Allis, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 18/338,411

(22) Filed: Jun. 21, 2023

(65) Prior Publication Data

US 2023/0332694 A1 Oct. 19, 2023

Related U.S. Application Data

(62) Division of application No. 16/514,183, filed on Jul. 17, 2019, now Pat. No. 11,725,741.

(60) Provisional application No. 62/699,022, filed on Jul. 17, 2018.

(51) Int. Cl.
| | |
|---|---|
| *F16K 11/07* | (2006.01) |
| *A61M 5/142* | (2006.01) |
| *A61M 39/22* | (2006.01) |
| *F16K 99/00* | (2006.01) |
| *G05D 7/01* | (2006.01) |

(52) U.S. Cl.
CPC ..... *F16K 11/0716* (2013.01); *A61M 5/14216* (2013.01); *A61M 39/223* (2013.01); *F16K 99/0011* (2013.01); *F16K 99/0057* (2013.01); *G05D 7/0153* (2013.01); *A61M 2039/224* (2013.01); *F16K 2099/0086* (2013.01)

(58) Field of Classification Search
CPC ............ A61M 5/14216; A61M 39/223; A61M 2039/224; F16K 11/0716; F16K 99/0011; F16K 99/0057; F16K 2099/0086
See application file for complete search history.

(56) References Cited

U.S. PATENT DOCUMENTS

| | | | | |
|---|---|---|---|---|
| 3,552,441 A | * | 1/1971 | Luhleich | F16K 11/065 138/155 |
| 5,147,323 A | * | 9/1992 | Haber | A61M 5/322 604/232 |

(Continued)

*Primary Examiner* — James D Ponton
*Assistant Examiner* — John A Doubrava
(74) *Attorney, Agent, or Firm* — Goodwin Procter LLP

(57) ABSTRACT

Disclosed are examples of valve systems and methods of operating the respective valve systems. An example valve system may include a valve body, an inlet component, an outlet component and a valve tube. The valve body may include a first void and a second void. The inlet component may be coupled to the first void and the outlet component may be coupled to the second void. The valve tube may include a side port and may be positioned through the valve body and coupled to the first void, the inlet component, the second void, and the outlet component. Other valve system examples may include including a valve body, a first septum, a second septum, a first piston, a second piston and a tube. The disclosed methods describe the interaction of the respective components of the respective valve system example.

11 Claims, 19 Drawing Sheets

(56) References Cited

U.S. PATENT DOCUMENTS

| | | | |
|---|---|---|---|
| 11,280,327 B2* | 3/2022 | Allis | F04B 7/0049 |
| 2015/0064036 A1* | 3/2015 | Eberhard | F04B 51/00 417/557 |

* cited by examiner

LOW FORCE VALVES FOR DRUG DELIVERY PUMPS

CROSS REFERENCE TO RELATED APPLICATION

This application is a division of U.S. application Ser. No. 16/514,183, filed Jul. 17, 2019, which claims priority to provisional application No. 62/699,022, entitled LOW FORCE VALVES FOR DRUG DELIVERY PUMPS, filed on Jul. 17, 2018, the entire contents of which are incorporated herein by reference.

BACKGROUND

Many conventional valves displace fluid when opening or closing by having a material or component intrude into a fluid path to close it. Such valves may include check valves, pinch valves, gate valves, and needle valves, as well as other common conventional valves. These types of valves may be made to be relatively low force and relatively small; however, these types of valves also may introduce dose accuracy issues as unintended fluid delivery may occur with each valve actuation.

Other types of valves that do not displace fluid when opening and closing are likely to be larger and of higher force. For example, rotary (stopcock) and shear valves use high compression seals (high force) to maintain seals. However, these valves typically use O-rings. Due to the tolerances of the O-rings at very small sizes, the force to actuate these valves may vary widely depending on the amount of compression on each O-ring.

It would be beneficial to have a valve that has low actuation force and does not displace fluid when operating to provide greater accuracy in dosing.

SUMMARY

Disclosed is an example of a valve system including a valve body, an inlet component, an outlet component and a valve tube. The valve body may include a first void and a second void. The inlet component may be coupled to the first void and the outlet component may be coupled to the second void. The valve tube may include a side port and may be positioned through the valve body and coupled to the first void, the inlet component, the second void, and the outlet component.

Disclosed is another example of a valve system including a valve body, an inlet component, an outlet component, and a valve tube. The valve body may include a first void and a second void. The inlet component may be coupled to the first void and the outlet component may be coupled to the second void. The valve tube include a side port and may be pierced through the valve body and coupled to the first void, the inlet component, the second void, and the outlet component. The valve tube may be operable to be moved to a first position within the valve body to align the side port to the inlet component when fluid stored in an external reservoir coupled to the inlet component is to be drawn into the valve system and provided to a pump chamber coupled to the valve tube, and wherein the valve tube is moved to a second position within the valve body to align the side port to the outlet component when fluid stored in the pump chamber is to be pushed out of the valve system and on to a fluid path component coupled to the outlet component.

Disclosed is yet another example of a valve system. The valve system including a valve body, a first septum, a second septum, a first piston, a second piston and a tube. The first septum may be positioned within the valve body. The second septum may be positioned with the valve body and aligned with the first septum. The first piston may be coupled to a first pump chamber and positioned on a first side of the aligned first septum and the second septum. The second piston may be coupled to a second pump chamber and positioned on a second side of the aligned first septum and the second septum. The tube may include a first side port, a second side port, and a center plug positioned between the first and second side ports. The tube may be positioned through the valve body and the first septum and the second septum and positioned between the first and second pistons. The first side port may be coupled to an inlet component portion of the tube. The second side port may be coupled to an outlet component portion of the tube. The inlet component portion may be coupled to a reservoir storing a fluid and the outlet component portion coupled to a fluid path component.

DETAILED DESCRIPTION

Various examples provide valves and/or valve systems that operate without displacing fluid. The provided valves may be operated with a low actuation force and may be made to be relatively small (e.g., on a micro or miniature scale) to accommodate use within a wearable drug delivery device or pump system. Other examples are also disclosed.

Disclosed herein are one or more valve systems, components, and methods of use that solve one or more drawbacks of conventional valves, including those drawbacks described above. The disclosed valves may be made small with relatively few pieces and may be used in a wearable drug delivery device (e.g., drug delivery pump) to provide a liquid drug to a user.

In various examples, the valves disclosed herein may use a septum or septa. The use of septa allows for the use of lower durometer materials than may be used with a conventional O-ring based pump system. Further, the amount of compression may be controlled by the diameter of the tube instead of the tube, the inner diameter (ID) and outer diameter (OD) of an O-ring, and the barrel.

Disclosed herein are exemplary low actuation force, micro/miniature, and no fluid displacement valves (and/or valve systems and/or methods of use involving the same). As described, the disclosed valves solve the issues related to traditional O-ring seals at the micro/miniature scale. Process limitations of molding do not allow the molding tolerances of O-rings to scale proportionally as size is reduced. This may lead to much wider ranges of compression and thus increased ranges of force to actuate an O-ring seal as the size of the valve is reduced. Compounding the issue is the need for multiple seals to create non-displacing valves (a valve that does not change volume when actuated).

In various examples, one or more examples of valves are described that may use a side ported tube pierced through a septum or septa to create a low force, non-displacement, micro-miniature valve. By piercing through the septum or septa, the amount of seal force is more controlled than with an O-ring.

Figure 1:
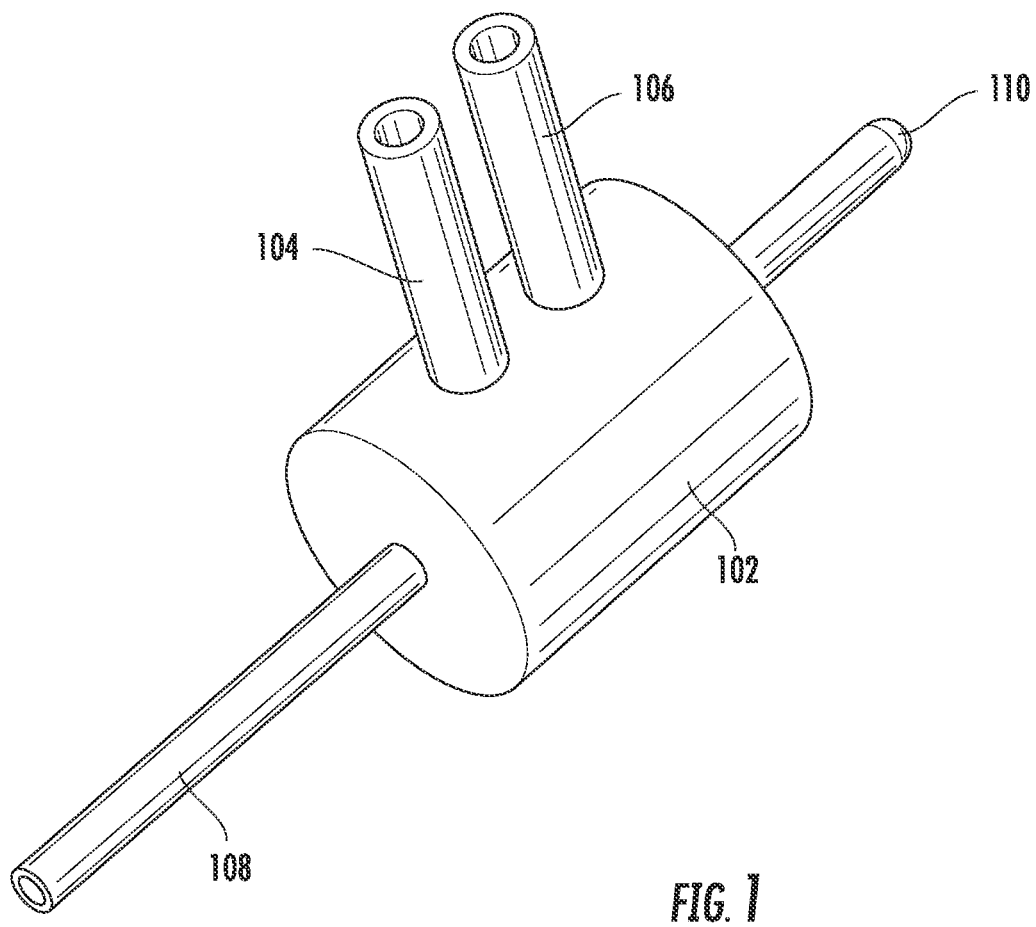
FIG. 1 illustrates a first exemplary valve system (or valve or valve component).

FIG. 1 illustrates a first exemplary valve system (or valve or valve component) 100. The valve system 100 may include a valve body 102, an inlet component 104, an outlet component 106, and a valve tube 108. The valve body 102 may be formed from silicone or may be formed from other compatible elastomeric material. The valve body 102 may be formed as a single molded piece or component, or as multiple molded pieces or components. The inlet component 104 may be a rigid tubing component that may be placed (as in a compression fit) into the valve body 102 or may be a tubing component bonded to the valve body 102. Similarly, in other examples, the outlet component 106 may be a rigid tubing component that may be placed into the valve body 102 or may be a tubing component bonded to the valve body 102. For example, the valve tube 108 may be a rigid tubing component. The valve tube 108 may be positioned (e.g., pierced) through the valve body 102 to create seals between the valve tube 108 and the inlet component 104 and/or the outlet component 106. The valve tube 108 may include an opening and may be moved back and forth within the valve body 102 as described further herein. The valve tube 108 may include a closed end 110. The closed end 110 may be crimped, welded, formed, capped, and/or filled.

Figure 2:
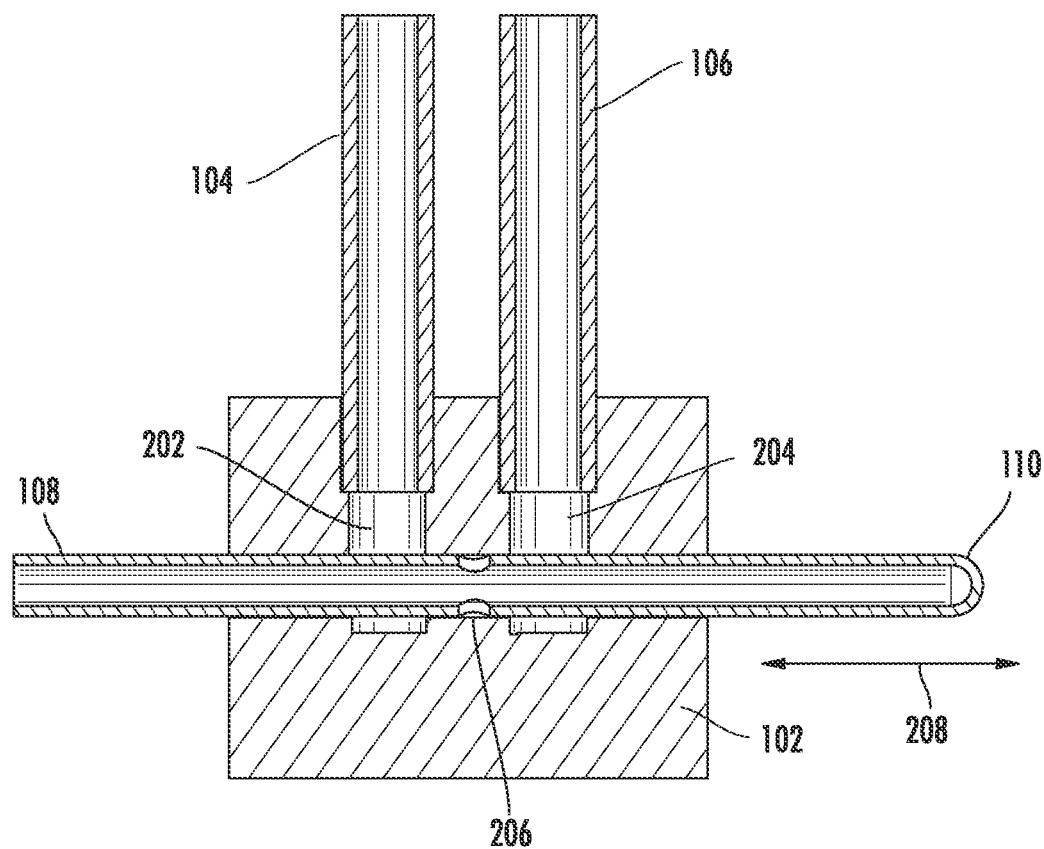
FIG. 2 illustrates a cross-sectional side view of the valve system.

FIG. 2 illustrates a cross-sectional side view of the valve system 100. As shown, the valve system 100 may include a first opening or void 202 and a second opening or void 204. The first void 202 may be coupled or connected to the inlet component 104. The second void 204 may be coupled or connected to the outlet component 106. As further shown, the valve tube 108 may include a side port 206. The side port 206 may comprise one or more openings (e.g., aligned openings) in the valve tube 108. The side port 206 may be formed using a grinding method, a laser cutting process, a machining process, or may be part of the original forming process for the valve tube 108 (e.g., through a molding process).

The valve body 102 may be considered to be a septum (or septa). As is shown in FIG. 2, the valve tube 108 may, for example, be pierced through the septum (e.g., valve body 102) stretching the septum over the valve tube 108 to create a seal. The valve body 102 may include the voids 202 and 204, connected to the inlet and outlet components 104 and 106, respectively, where no seal to the valve tube 108 is provided. The valve tube 108 may be connected to a pump head (not shown in FIG. 2) that may either draw a fluid in through the side port 206 (from the inlet component 104) or push the fluid out through the side port (through the outlet component 106). The valve system 100 may function by being operable to move the side port 206 of the valve tube 108 between the voids 202 and 204 to connect and disconnect the pump head from the inlet and outlet components 104 and 106 as appropriate. In various examples, a pump (not shown in FIG. 2) could also or alternatively be coupled to the valve tube 108.

A direction of movement of the valve tube 108 within the valve body 102 is shown by 208. As shown, the valve tube 108 may be moved linearly in the directions shown by 208 through the valve body 102. The movement of the valve tube 108 may cause the side port 206 to change between being exposed to the inlet component 104 and the outlet component 106. When transitioning between the inlet component 104 and the outlet component 106, the side port 206 may be completely closed off from the inlet component 104 and the outlet component 106 to prevent any unintended flow of fluid.

In various examples, the valve system 100 may be used within or as part of a drug delivery device including, for example, a wearable drug delivery device. In various examples, the inlet component 104 may be coupled to a reservoir storing a liquid drug or any liquid therapeutic agent (or any fluid). In various examples, the outlet component 106 may be coupled to fluid path (e.g., including a cannula) that is coupled to a user or patient such that the liquid drug stored in the reservoir may be delivered to the user. In various examples, the liquid drug may be insulin and the valve system 100 may be part of a wearable insulin drug delivery device or system.

In various examples, the valve system 100 may be operable to pump in and/or pump out fluid without unintended fluid flow by maintaining a constant volume during transitions of coupling the side port 206 to either the inlet component 104 or the outlet component 106. In various examples, the valve system 100 may be applied to a fluid path requiring various path separations. In various examples, the valve system 100 may include dual inlets and a single outlet and/or more voids or open spaces may be added to increase the number of valve stations. Any number of voids, valve stations, inlet, and/or outlet components may be accommodated.

Figure 3:
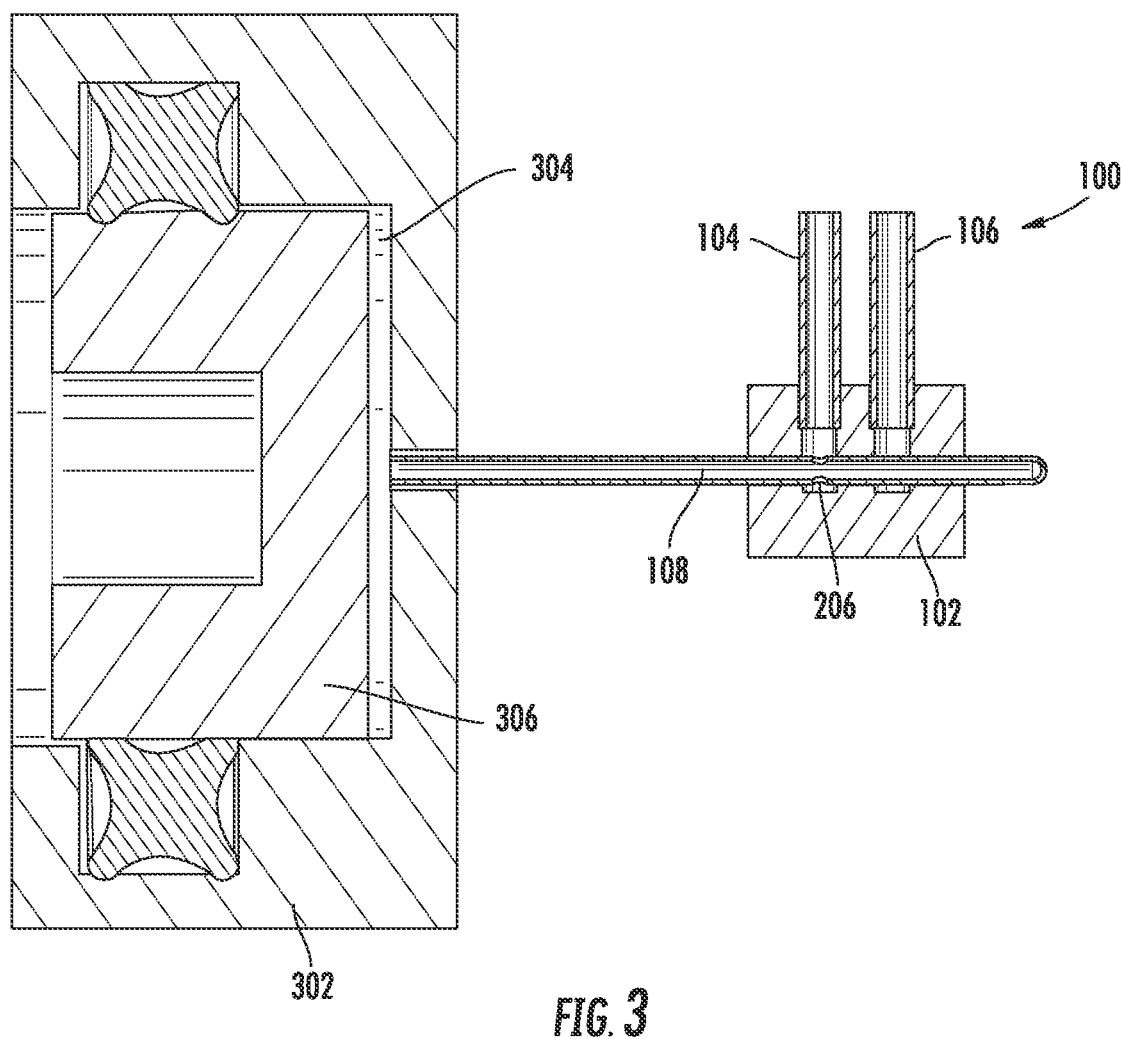
FIG. 3 illustrates a delivery system (or pump or valve delivery system).

FIG. 3 may represent a cross-sectional side view of a delivery system 300. As shown in FIG. 3, the delivery system 300 may include the valve system 100. The delivery system 300 may further include a pump head component 302 coupled to the valve system 100. The pump head component 302 may include a pump chamber 304 and a pump piston 306.

FIG. 3 illustrates the delivery system 300 in a first or initial stage of operation. As shown, the delivery system 300 is ready to fill the pump chamber 304 with a fluid. The valve tube 108 may be coupled to the pump chamber 304. The inlet component 104 may be coupled to a reservoir storing the fluid (not shown in this example). The outlet component 106 may be coupled to a cannula and/or other fluid path that is coupled to a user. The side port 206 is aligned with/open to the inlet component 104 and is closed to the outlet component 106.

Figure 4:
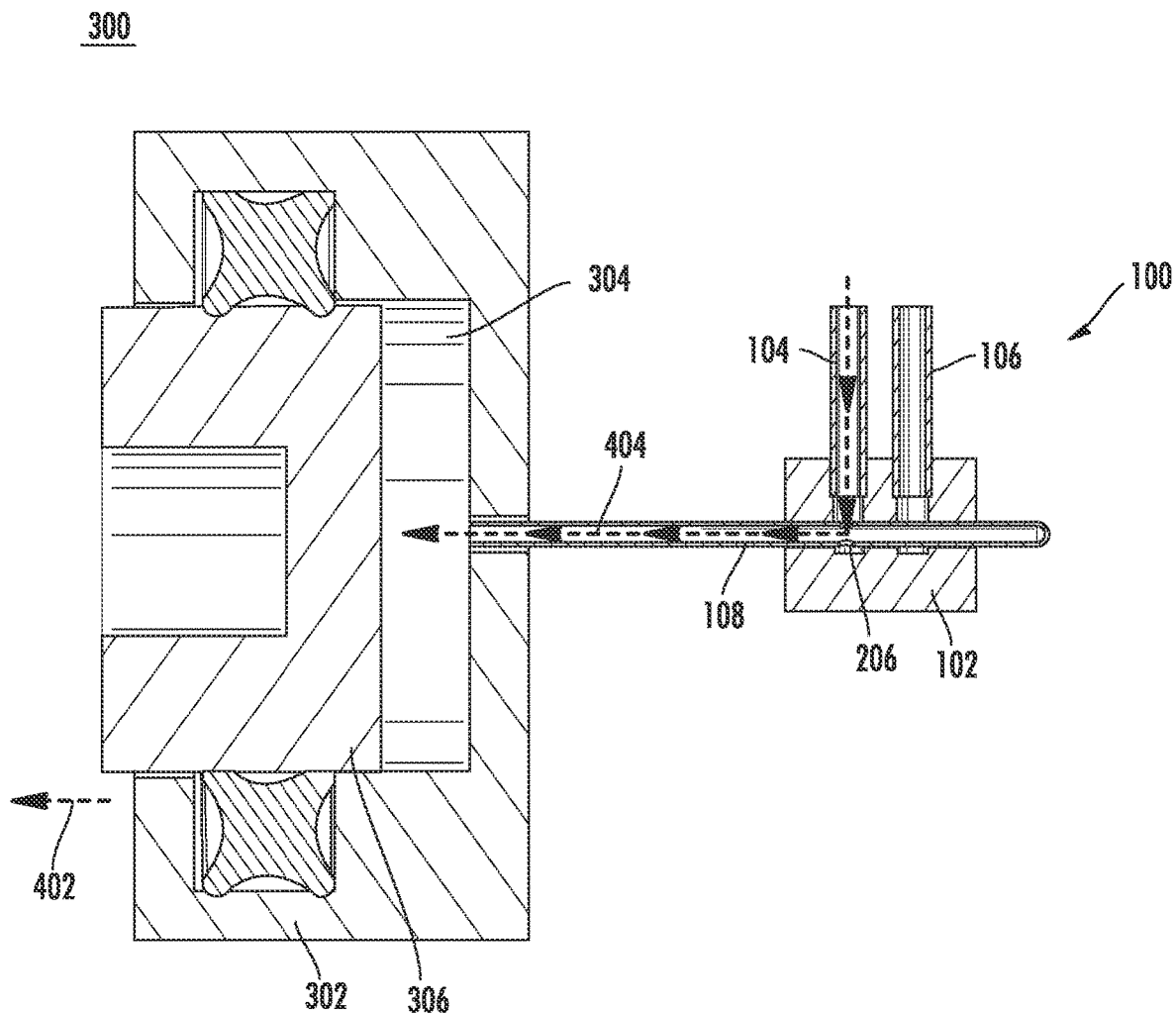
FIG. 4 illustrates a second stage of operation of the delivery system shown in FIG. 3.

FIG. 4 illustrates a second stage of operation of the delivery system 300 (subsequent to the stage of operation of the delivery system 300 as shown in FIG. 3). For example, the valve tube 108 may be operable to move to a first position within the valve body 102 to align the side port 206 to the inlet component 104 when fluid is available to the inlet component (e.g., fluid may be stored in an external reservoir (not shown) coupled to the inlet component) is to be drawn into the inlet component. As shown in FIG. 4, the pump piston 306 is moved in a direction 402. The movement of the pump piston 306 causes fluid to be drawn into the pump chamber 304—through the inlet component 104, through the valve tube 108, and into the pump chamber 304—as shown by arrow flow indicators 404. As a result, all or a portion of the pump chamber 304 may be filled with the fluid. The pump piston 306 may operable to be moved by any suitable actuation system.

Figure 5:
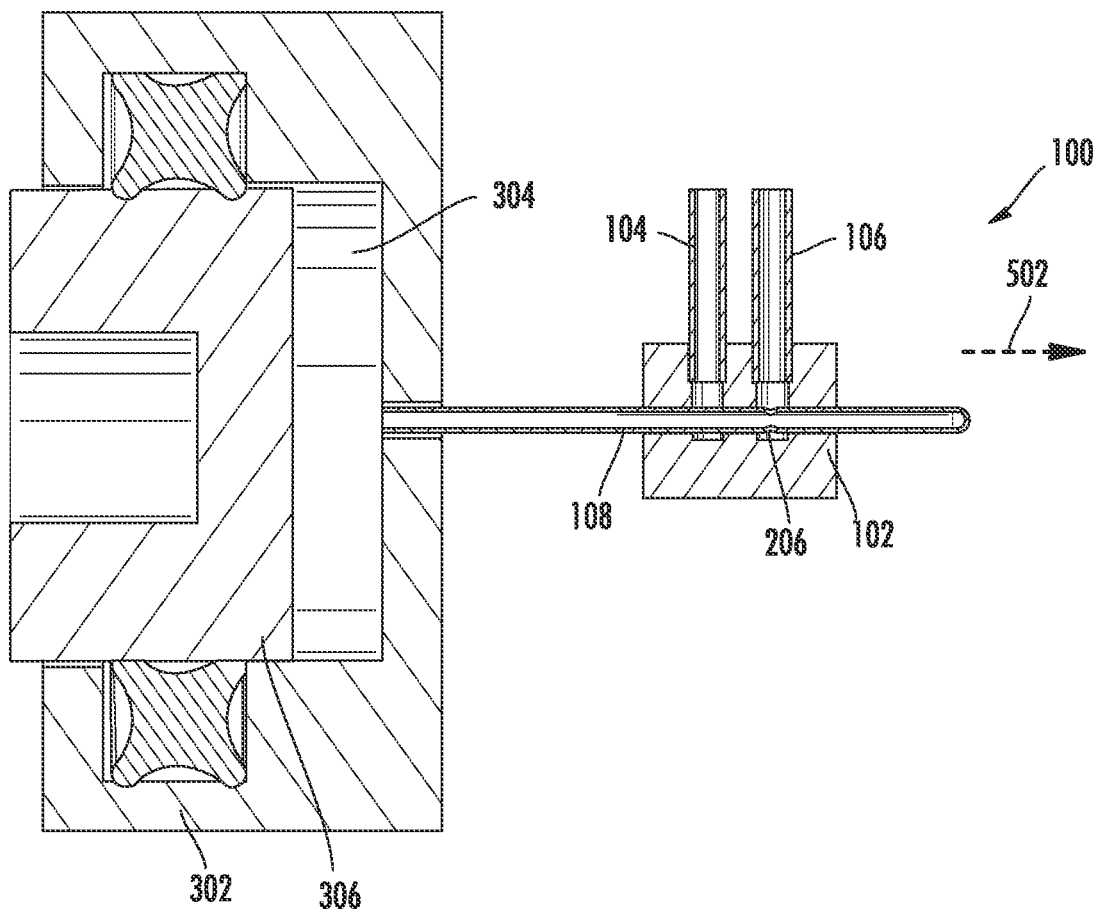
FIG. 5 illustrates a third stage of operation of the delivery system shown in FIG. 4.

FIG. 5 illustrates a third stage of operation of the delivery system 300 (subsequent to the stage of operation of the delivery system 300 as shown in FIG. 4). As shown in FIG. 5, the valve tube 108 is operable to move in a direction 502. The movement of the valve tube 108 may cause the side port 206 to be aligned with/open to the outlet component 106 (e.g., at a second position) and be closed to the inlet component 104.

Figure 6:
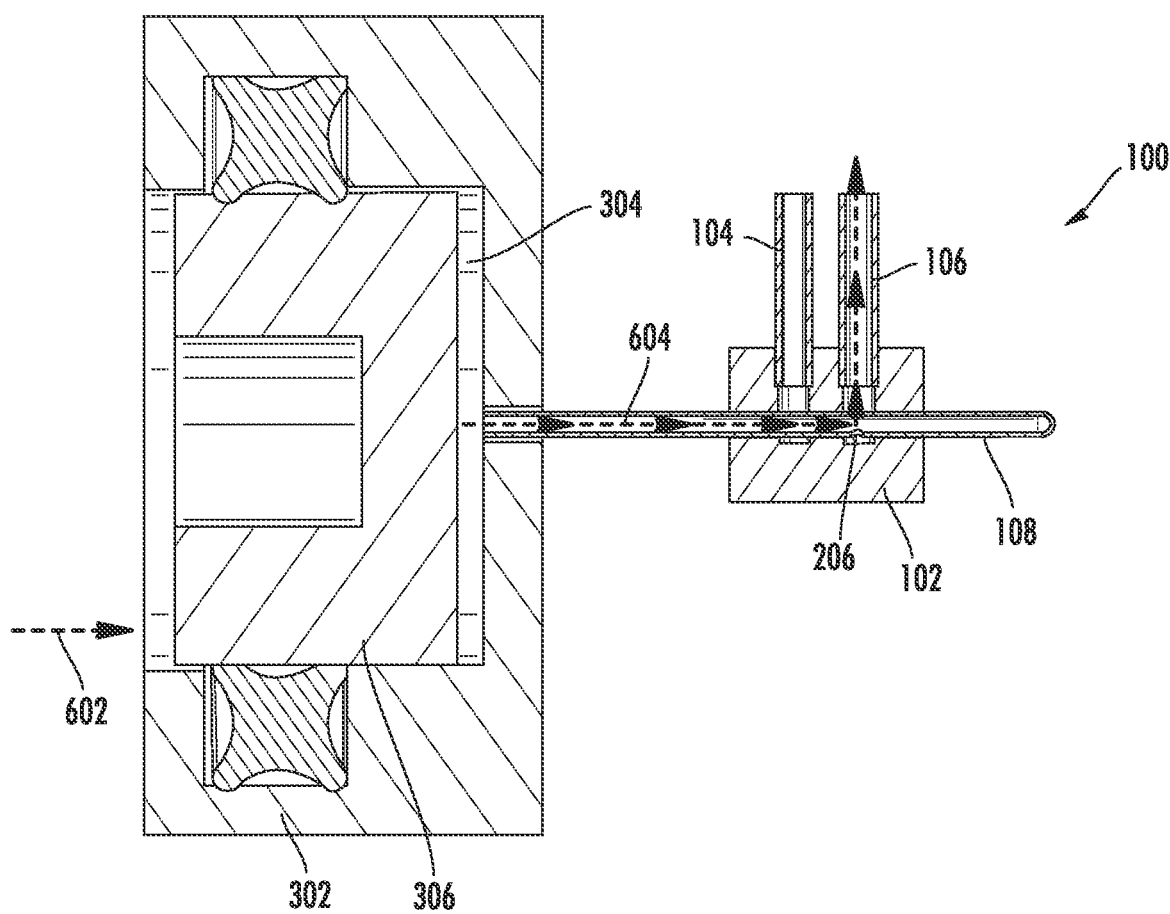
FIG. 6 illustrates a fourth stage of operation of the delivery system 300 shown in FIG. 5.

FIG. 6 illustrates a fourth stage of operation of the delivery system 300 (subsequent to the stage of operation of the delivery system 300 as shown in FIG. 5). As shown in FIG. 6, the pump piston 306 is moved in a direction 602 that aligns the side port 206 with outlet component 106. The movement of the pump piston 306 causes fluid to be pushed in the direction (shown by directional arrows 604) from the pump chamber 304 for delivery—i.e., from the pump chamber 304, through the valve tube 108, and through the outlet component 106 (as indicated by the directional arrows 604) (and on to a cannula and/or fluid path for delivery to the user).

Figure 7:
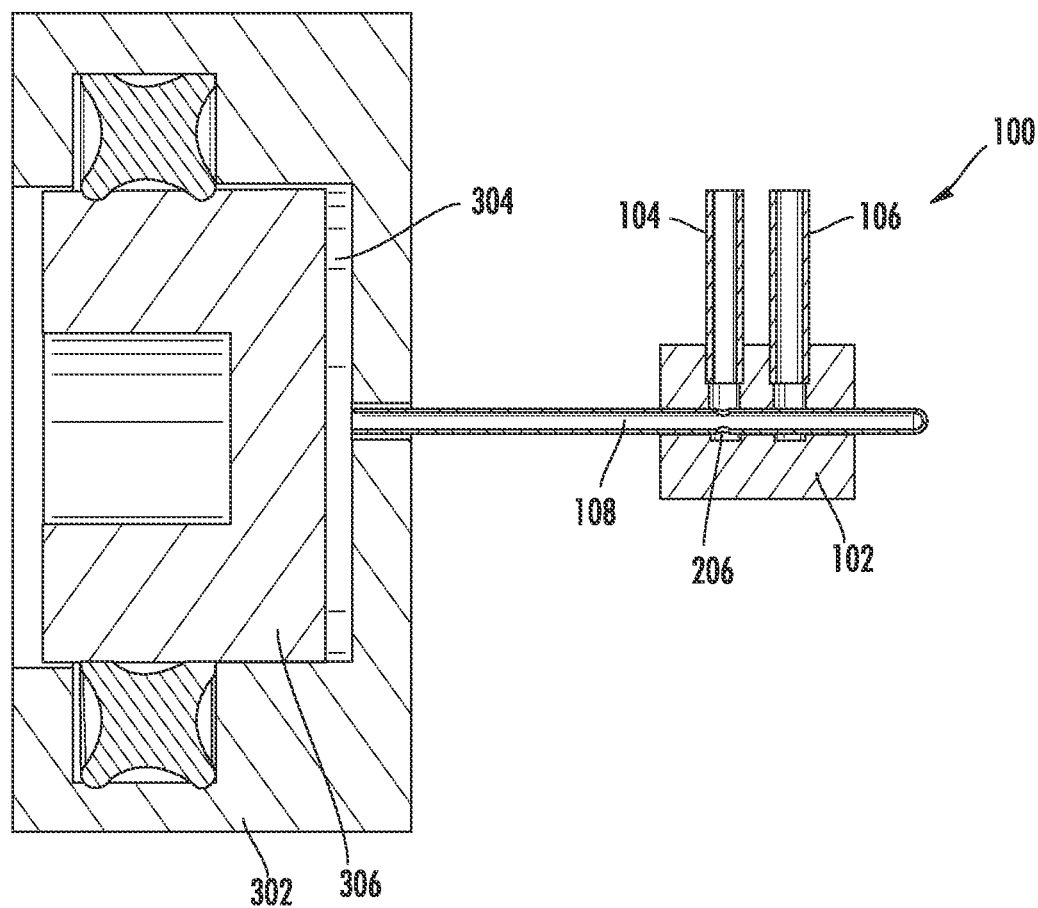
FIG. 7 illustrates a fifth stage of operation of the delivery system shown in FIG. 6.

FIG. 7 illustrates a fifth stage of operation of the delivery system 300 (subsequent to the stage of operation of the delivery system 300 as shown in FIG. 6). As shown in FIG. 7, the side port 206 is realigned with the inlet component 104 to return to the state of operation shown in FIG. 3. The delivery system 300 may repeat the steps illustrated in FIGS. 3-7 (or a portion thereof) to implement a subsequent cycle of drawing in the fluid to the pump chamber 304 from the reservoir and pushing it out for delivery to a patient.

As an alternative to moving the valve tube 108, the valve body 102 may be moved along the valve tube 108 to align the side port 206 appropriately with the outlet component 106. For example, the valve body 102 may be configured and operable to be moved to a first position with respect to the valve tube 108 to align the side port 206 to the inlet component 104 when fluid is available to the inlet component 104 (e.g., stored in an external reservoir coupled to the inlet component 104) to be drawn into the inlet component 104. The valve body 102 may be configured and operable to be moved to a second position with respect to the valve tube 108 to align the side port 206 to the outlet component 106 when fluid is to be pushed out of the valve system 100 to the outlet component 106 for delivery of the fluid. The valve tube 108 and/or the valve body 102 may be moved by any suitable actuation system.

Figure 8:
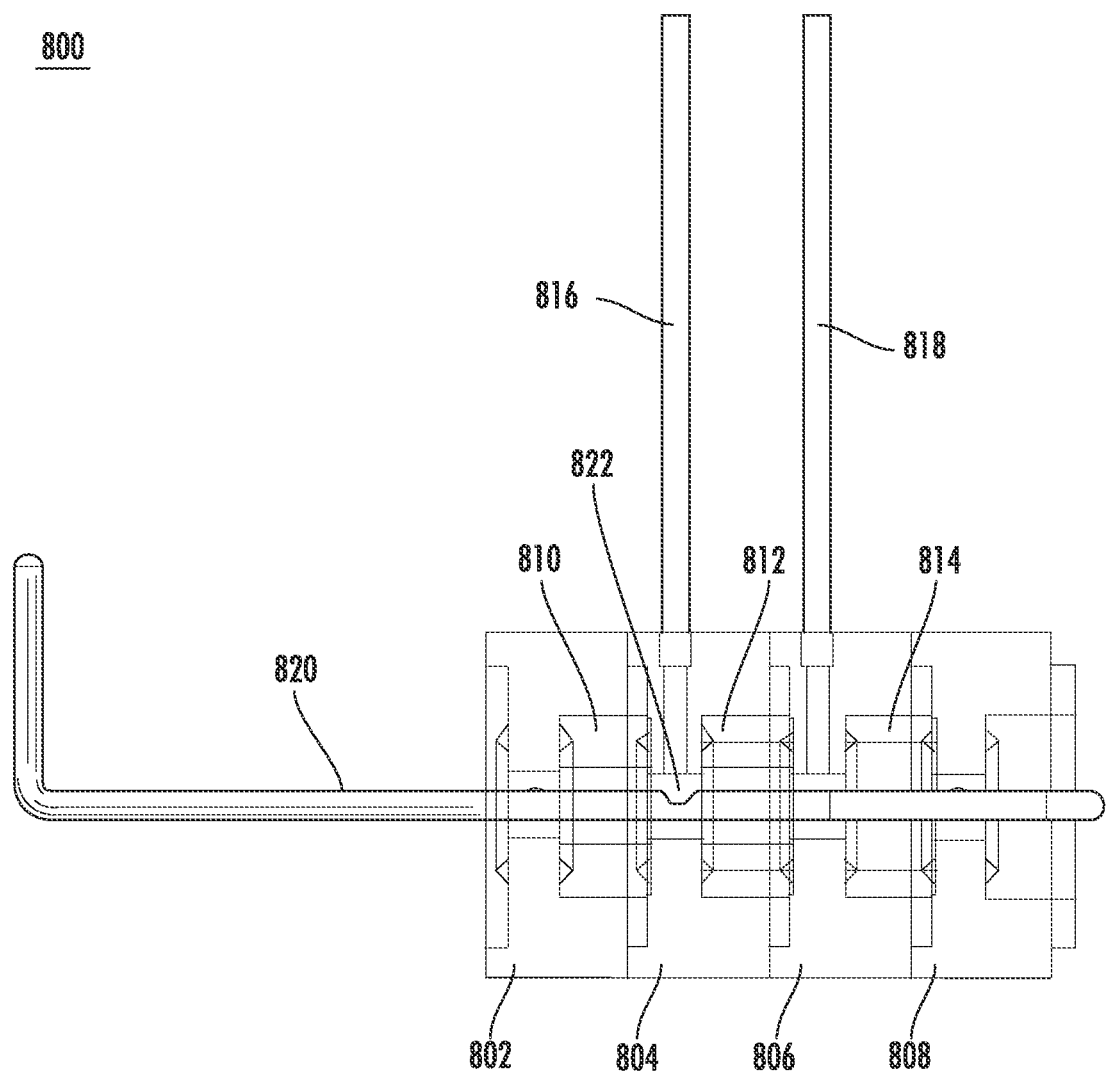
FIG. 8 illustrates a second exemplary valve system.

FIG. 8 illustrates a second exemplary valve system (or valve or valve component) 800. As shown in FIG. 8, the valve system 800 may include a first seal body component 802, a second seal body component 804, a third seal body component 806, and a fourth seal body component 808. Positioned between the seal body components may be a first septum 810, a second septum 812, and a third septum 814. The valve system 800 may further include an inlet component 816, an outlet component 818, and a valve tube 820. The valve tube 820 may include an opening 822. The inlet component 816 may, for example, be coupled to a reservoir. The outlet component 818 may, for example, be coupled to a fluid path coupled to a user.

The valve system 800 may be coupled to a pump head (not shown in FIG. 8) that may be used to draw in and push out fluid in a manner similar to the operation of valve system 100. The valve tube 820 may be moved through the septa 810-814 and the openings/air cavities of the seal body components 802-808 to couple the opening 822 to the inlet component 816 or to the outlet component 818 to draw in fluid from a reservoir and/or push out fluid for delivery to a user.

Figure 9:
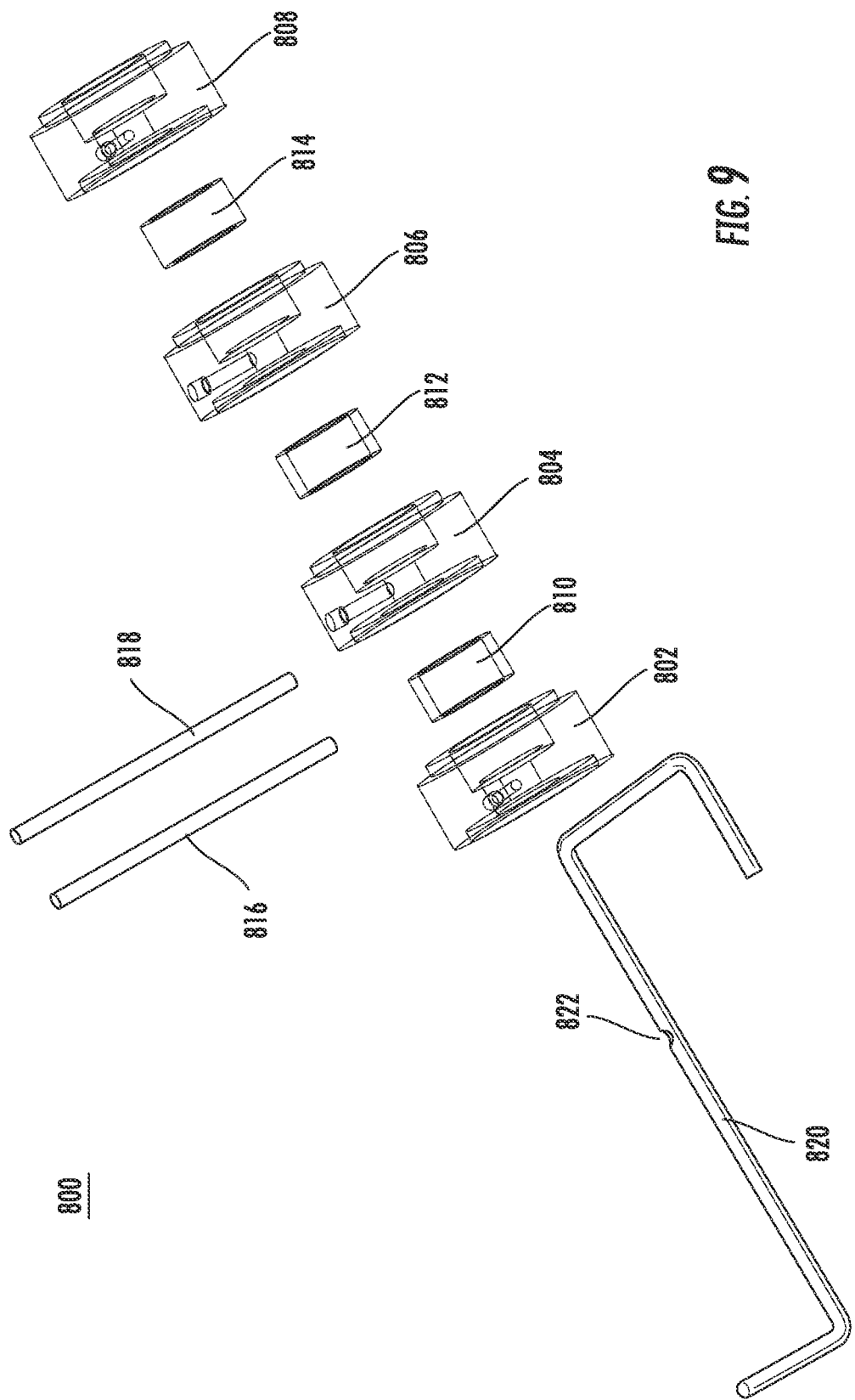
FIG. 9 illustrates an exploded view of the valve system of FIG. 8.

FIG. 9 illustrates an exploded view of the valve system 800. FIG. 9 shows the arrangement of the components of the valve system 800. The seal bodies 802-808 may be rigid components. The septa 810-814 may be a soft material and/or compressible material. The seal bodies 802-808 may be arranged such that the interior openings or cavities may be aligned. The valve tube 820 may be of any shape and may be positioned through the openings of the seal bodies 802-808 and the septa 810-814.

Figure 10:
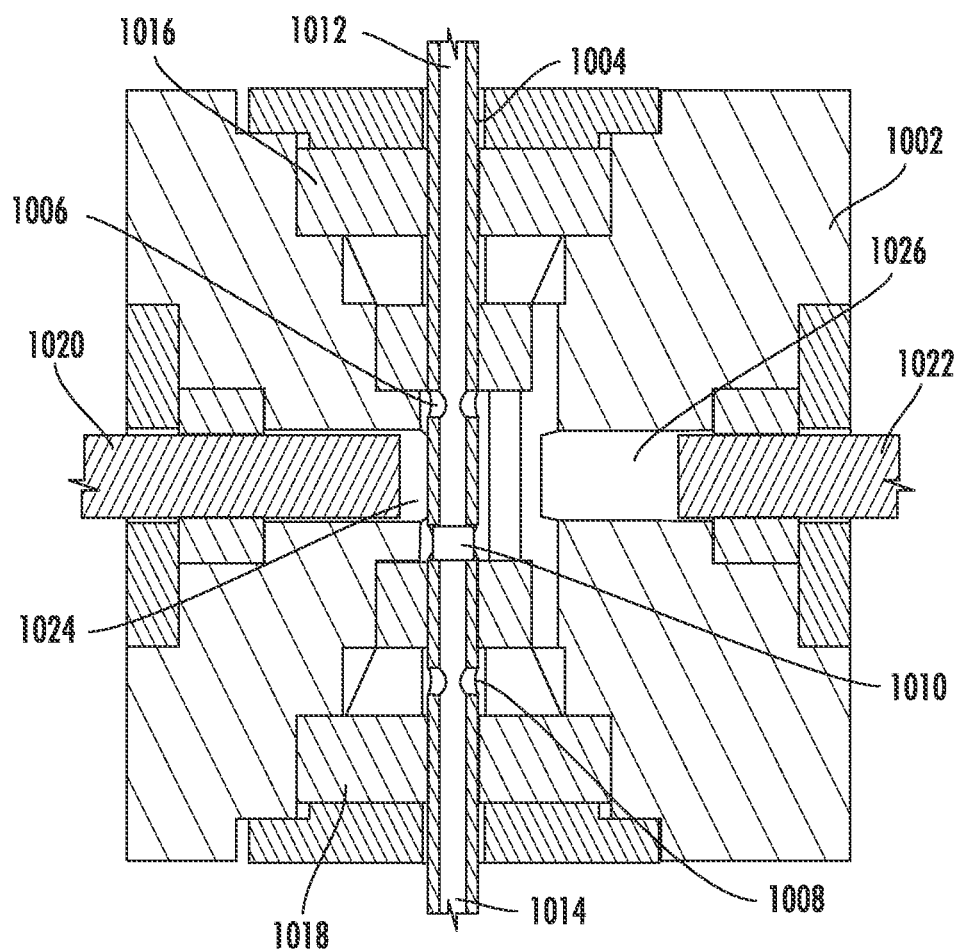
FIG. 10 illustrates a third exemplary valve system (or valve or valve component).

FIG. 10 illustrates a third exemplary valve system 1000. As shown in FIG. 10, the valve system 1000 includes a valve body 1002 and a side ported tube component 1004. The valve body 1002 may be formed by injection molded thermoplastic. The side ported tube 1004 may include a first opening or side port 1006, a second opening or side port 1008, and a plug 1010. The side ported tube 1004 may be a rigid tubing placed into the valve body 1002. The valve body 1002 may be considered to be a pump block of the valve system 1000.

The plug 1010 may be installed into the tube 1004 as a separate piece or component from the tube 1004 or may be formed through spot-weld process, a crimping process, a swaging process, a filling/plugging process, any combination thereof, or the like. A first portion of the tube 1004 may be or may form an inlet component 1012 of the tube 1004. A second portion of the tube 1004 may be or may form an outlet component 1014 of the tube 1004. The plug 1010 may help prevent fluid flowing through (e.g., by a liquid drug) between the inlet component 1012 and the outlet component 1014. As with the other examples disclosed herein, the inlet component 1012 may be coupled to a reservoir storing a liquid drug or other therapeutic agent and the outlet component 1014 may be coupled to a fluid path (e.g., a cannula) coupled to a patient.

In various examples, the tube 1004 may be formed of two or more tubes. For example, the tube 1004 may be formed of two separate tubes having end caps joined together to form the plug 1010 and capable of moving together as a single component.

As further shown in FIG. 10, the valve system 1000 may further include a first septum component 1016 and a second septum component 1018. The first septum 1016 and the second septum 1018 may each be formed from liquid silicone rubber or other compatible elastomeric material. The first septum 1016 and the second septum 1018 may each be formed (e.g., molded) as a single component or piece or as multiple components or pieces. The first septum 1016 and the second septum 1018 may each be pierced by the tube 1004. The valve system 1000 may further include a first piston 1020 (e.g., a left piston based on the orientation of the valve system 1000 as depicted in FIG. 10) and a second piston 1022 (e.g., a right piston based on the orientation of the valve system 1000 as depicted in FIG. 10). The first and second pistons 1020 and 1022 may be moved (e.g., linearly) within a first piston pump chamber 1024 and a second piston pump chamber 1026, respectively.

In various example, components of the valve system 1000 may be arranged in a symmetrical manner. For example, the first septum 1016 and the second septum 1018 may be aligned along a first axis and the pistons 1020 and 1022 may be aligned along a second axis, perpendicular to the first axis.

The arrangement of the components of the valve system 1000 may form a low force, non-displacement, micro/miniature valve. The valve system 1000 may provide a cross-flow valve that provide a two position, four-way ported valve that may alternatively connect the pump chambers 1024 and 1026 to the inlet component 1012 and the outlet component 1014 of the valve body 1002. By providing the tube 1004 to pierce through the septa 1016 and 1018, the amount of seal force may be more controlled than with an O-ring as described herein.

In various examples, the septa 1016 and 1018 may form radial seals with the valve body 1002. Each septum 1016 and 1018 may include two radial sealing faces to the valve body 1002 separated with an opening or through-hole (e.g., a void) where no seal to the tube 1004 is provided. The voids may create openings that may provide fluid channels to the side ported tube 1004.

The voids and design of the valve body 1002 may create separate fluid channels coupling the piston pump chambers 1024 and 1026 and the inlet and outlet components 1012 and 1014, based on the position of the valve tube 1004. The valve system 1000 may operate by actuating/moving the side ported tube 1004 to the correct position along each septum 1016 and 1018 prior to movement of the pistons 1020 and 1022 (e.g., prior to a stroke of the pistons 1020 and 1022), thereby appropriately connecting and/or disconnecting the proper piston 1020 and 1022 from the inlet or outlet component 1012 and 1014 as described in more detail herein.

Figure 11:
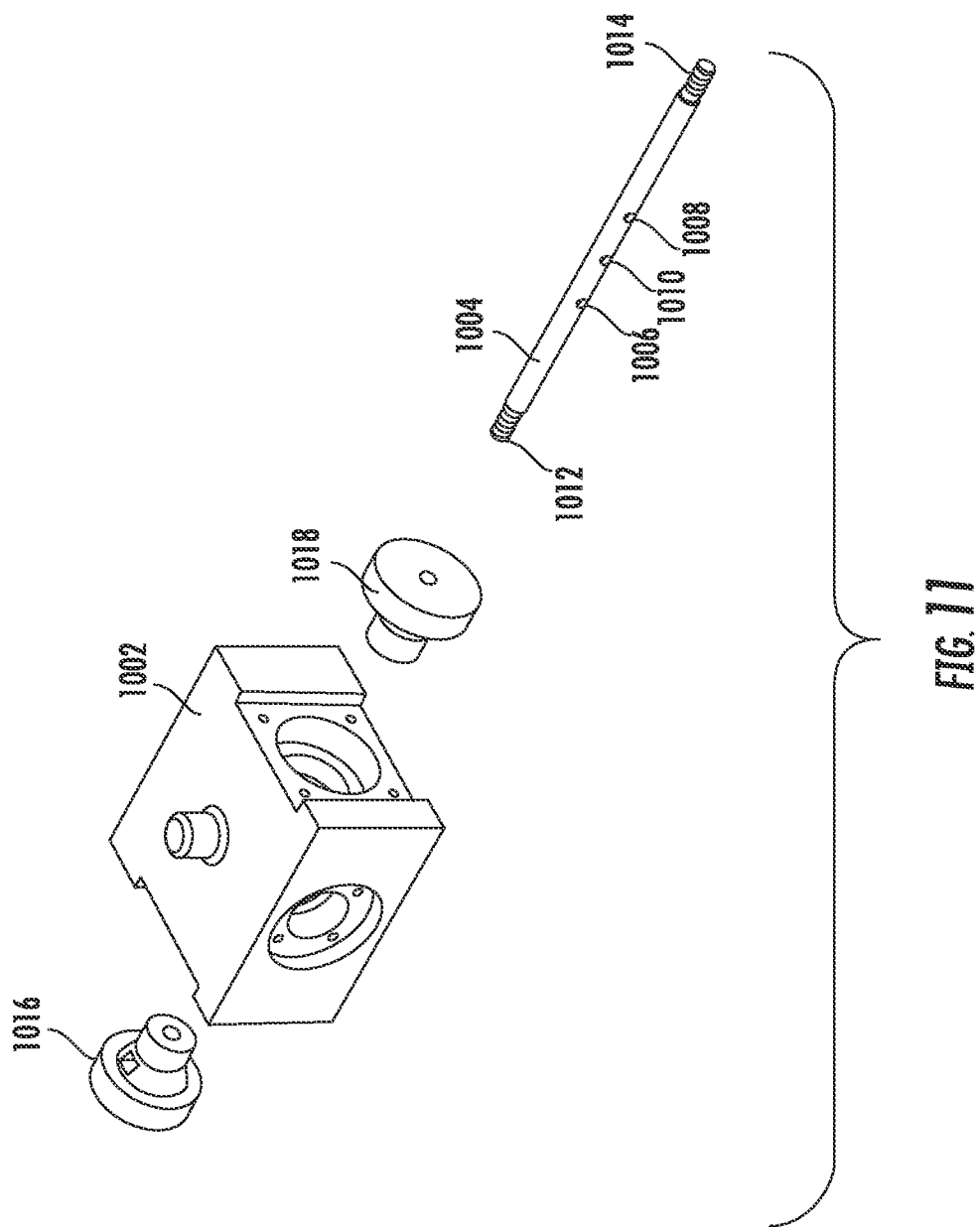
FIG. 11 illustrates an exploded view of a portion of the valve system.

FIG. 11 illustrates an exploded view of a portion of the valve system 1000. Specifically, FIG. 11 illustrates an arrangement of the pump block 1102, the septa 1016 and 1018, and the side ported tube 1004 (the side ported tube 1004 may also be referred to as a needle). The septa 1016 and 1018 are each represented as single piece components. The side ported tube 1004 may be installed through the septa 1016 and 1018.

In various examples, the valve body 1002 and the septa 1016 and 1018 may be stationary or held fixed as the side ported tube 1004 is actuated or moved. The side ported tube 1004 may be moved linearly through the septa 1016 and 1018 and the valve body 1002. Linear actuation of the tube 1004 allows the side ports 1006 and 1008 to change connections between the piston pump chambers 1024 and 1026 (not shown in FIG. 11) and the inlet and outlet components 1012 and 1014. Because the tube 1004 is plugged by plug 1010 between the two side ports 1006 and 1008, there is no connection between the inlet component 1012 and outlet component 1014 of the tube 1004 during operation which prevents unintended drug delivery.

Figure 12:
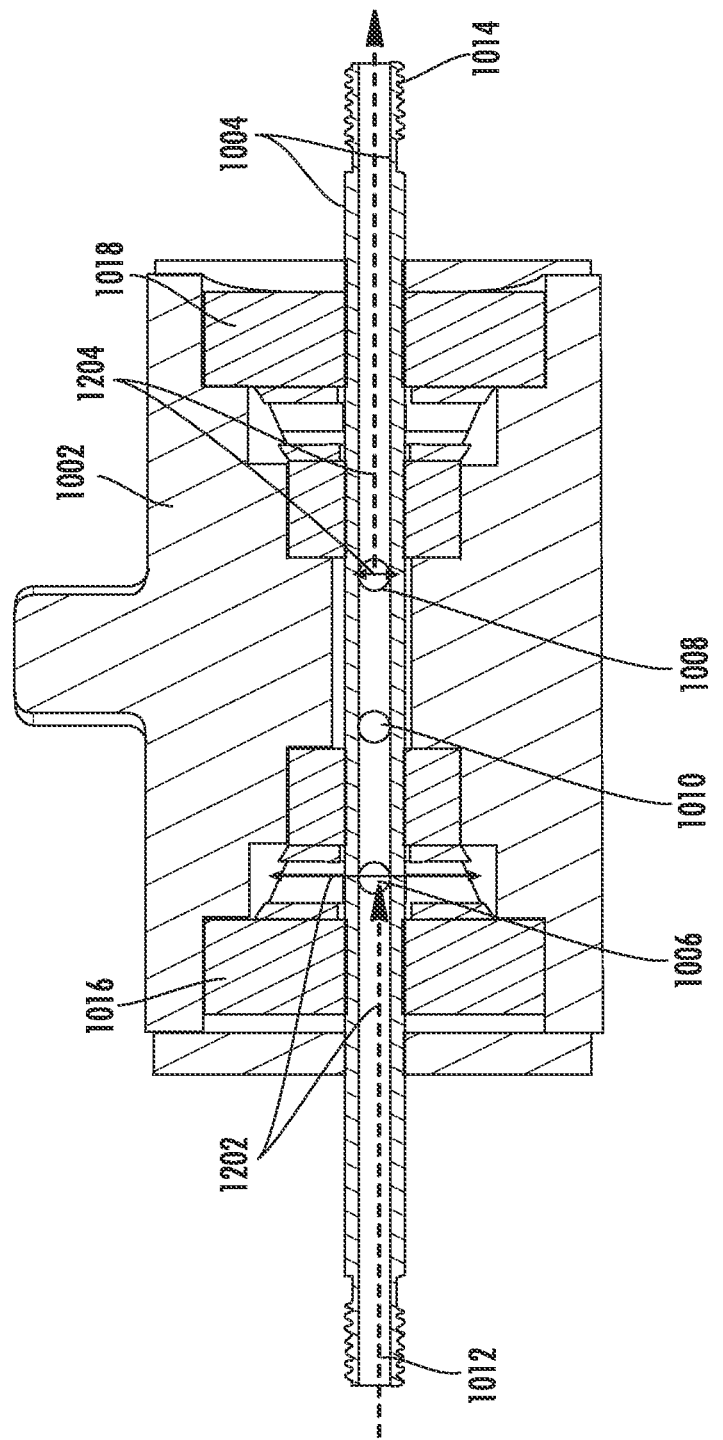
FIG. 12 illustrates a cross-sectional side view of a portion of the valve system depicted in FIG. 11.

FIG. 12 illustrates a cross-sectional side view of a portion of the valve system 1000 (e.g., the portion of the valve system 1000 depicted in FIG. 11). FIG. 12 shows the fluid path provided within the valve system 1000 between the side ported tube 1004 and the piston pump chambers 1024 and 1026 (not shown in FIG. 12). The design and arrangement of the septa 1016 and 1018 (relative to the design and arrangement of the valve body 1002 and/or other components of the valve system 1000) may provide fluidic connections between channels within the valve body 1002 and the channel provided by the tube 1004 (e.g., the internal open areas of the tube 1004). The septa 1016 and 1018 also provide for two distinct face seals with the valve body 1002 to prevent any fluid from leaking from the valve system 1000. In turn, this allows the side ported tube 1004 to have access to the pump chambers 1024 and 1026.

As shown in FIG. 12, based on the position of the tube 1004, the side port 1006 may be coupled to the pump chamber 1026. As such, fluid may be drawn into the valve system 1000 (e.g., from an external reservoir or other fluid holding device) from the inlet component 1012 and through the side port 1006 as shown by flow arrows 1202. The flow arrows 1202 show that fluid may be drawn into the pump chamber 1026 and any channel in the valve body 1002 coupled to the pump chamber 1026.

Further, based on the position of the tube 1004, the side port 1008 may be coupled to the pump chamber 1024. As such, fluid may be pushed out of the valve system 1000 (e.g., to an external fluid path and/or cannula coupled to a patient) from the side port 1008 to the outlet component 1014 as shown by flow arrows 1204. The flow arrows 1204 show that fluid may be pushed out of the pump chamber 1024 and any channel in the valve body 1002 coupled to the pump chamber 1024.

Figure 13:
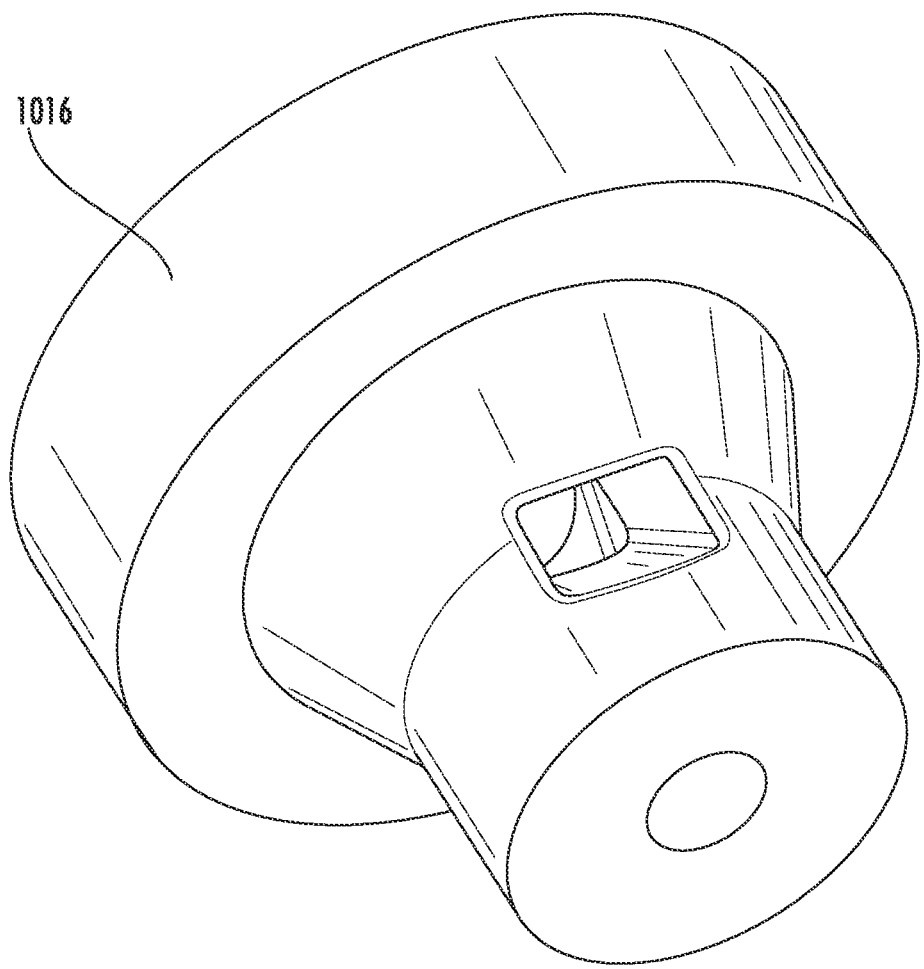
FIG. 13 illustrates a close-up view of an exemplary septum of the valve system.

FIG. 13 illustrates a close-up view of an example septum of the valve system 1000—for example, the septum 1016.

Figure 14:
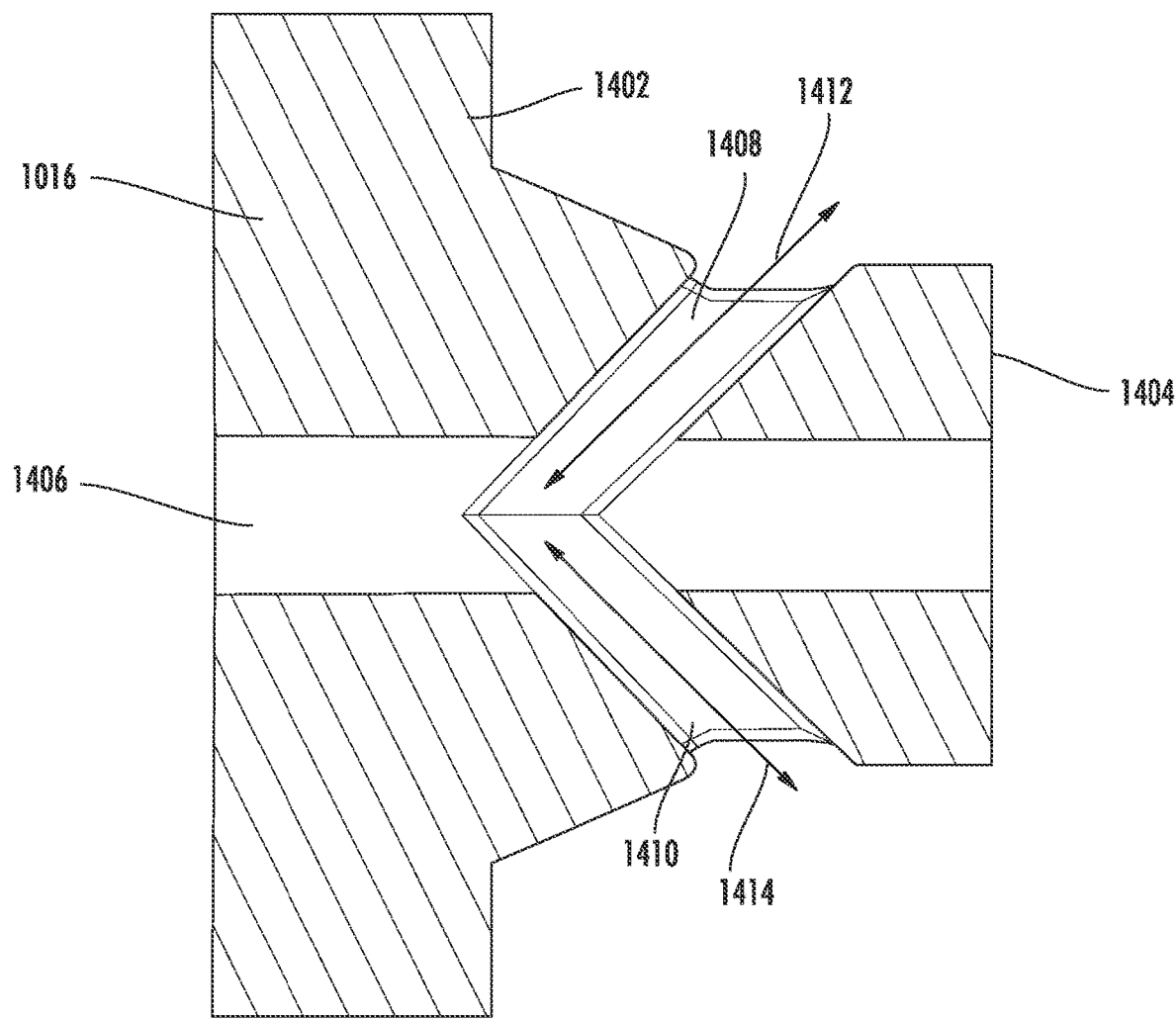
FIG. 14 illustrates a cross-sectional side view of an exemplary septum of the valve system, such as the septum example depicted in FIG. 13.

FIG. 14 illustrates a cross-sectional side view of an exemplary septum of the valve system 1000—for example, the septum 1016 depicted in FIG. 13. As shown in FIG. 14, the septum 1016 may include a first radial face seal 1402 (to the valve body 1002) and a second radial face seal 1404 (also to the valve body 1002). Further, the septum 1016 may include an inner open area or channel 1406 as well as a first angled opening or channel 1408 and a second angled opening or channel 1410 coupled to the inner channel 1406. Fluid may flow bidirectionally through the channel 1408 as indicated by flow indicator 1412 into the side ported tube 1004 depending on the position of the tube 1004. Similarly, fluid may flow bidirectionally through the channel 1410 as indicated by flow indicator 1414 into the side ported tube 1004 depending on the position of the tube 1004.

Figure 15:
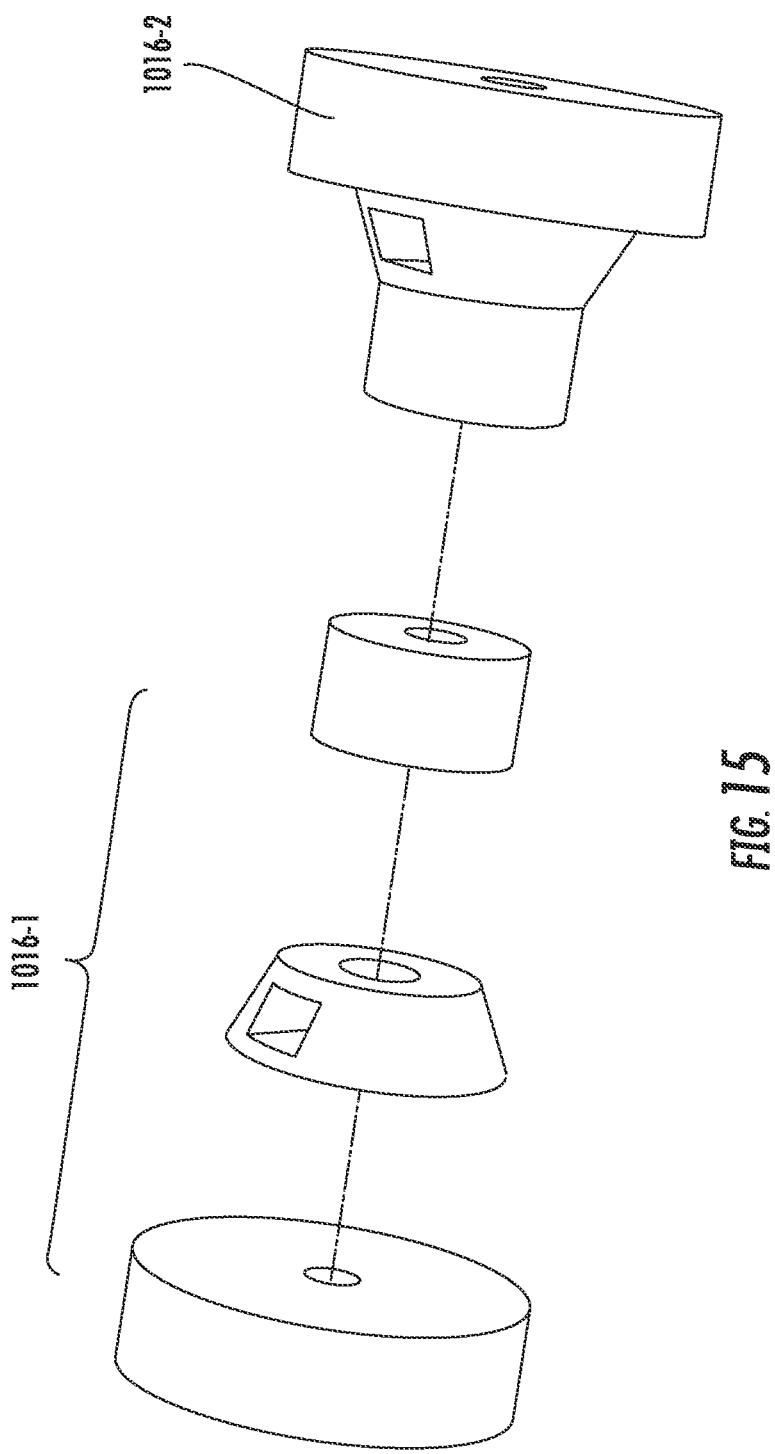
FIG. 15 illustrates alternative configurations of an example septum of the valve system such as the example septum depicted in FIG. 13.

FIG. 15 illustrates example configurations of an exemplary septum of the valve system 1000—for example, the septum 1016. Septum 1016-1 illustrates the septum 1016 formed as multiple pieces or components. Septum 1016-2 illustrates the septum 1016 formed as a single piece or component.

FIGS. 16-19 illustrate operation of the valve system 1000. Specifically, FIGS. 16-19 illustrate a sequence of operations for drawing in and pumping out a portion of a fluid by the valve system 1000 for delivery to a patient.

Figure 16:
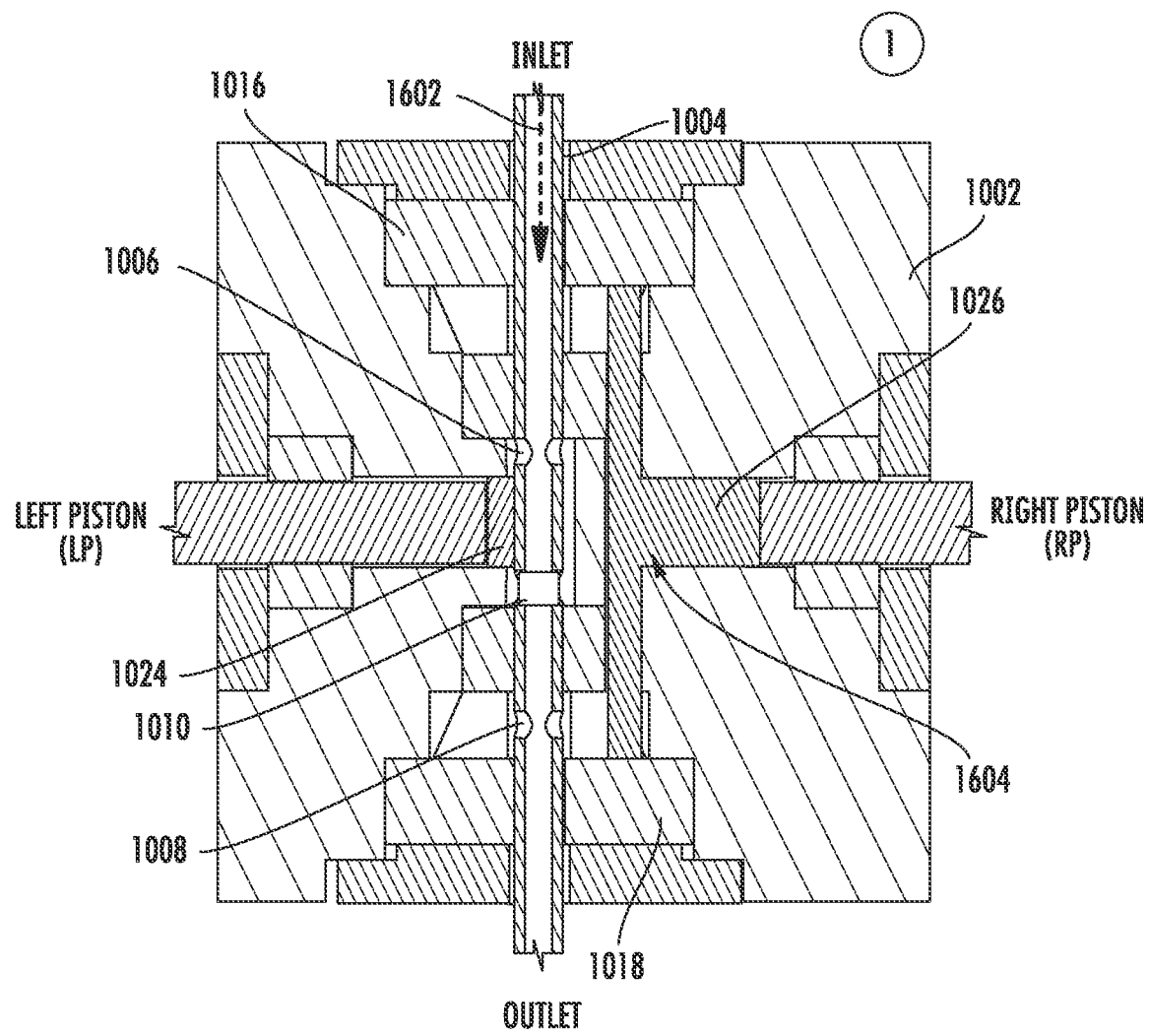
FIGS. 16-19 illustrate example operations of the valve system depicted in FIG. 11.

FIG. 16 illustrates the valve system 1000 in a first or initial stage of operation. As part of a first step in the sequence of operations, the tube 1004 is actuated to move in a direction 1602 to set the side ports 1006 and 1008 in appropriate positions for valving. Specifically, the tube 1004 is moved to position the side port 1006 (i.e., the side port connected to the inlet component 1012) to be coupled to the piston 1020/piston pump chamber 1024 (e.g., the left side piston as indicated in FIG. 16). Further, the side port 1008 (i.e., the side port coupled to the outlet component 1014) is positioned to be coupled the second piston 1022/piston pump chamber 1026. The side ports 1006 and 1008 may be coupled to the piston pump chambers 1024 and 1026, respectively, through the flow channels in the septa 1016 and 1018 as described herein. As shown in FIG. 16, a portion of a fluid 1604 is positioned in the valve system 1000 and occupies a portion of the flow channels formed in and/or coupled to the septa 1016 and 1018 and the piston pump chamber 1026. The piston pump chamber 1024 (and any coupled channel) may be empty or devoid of any, or substantially any, fluid.

Figure 17:
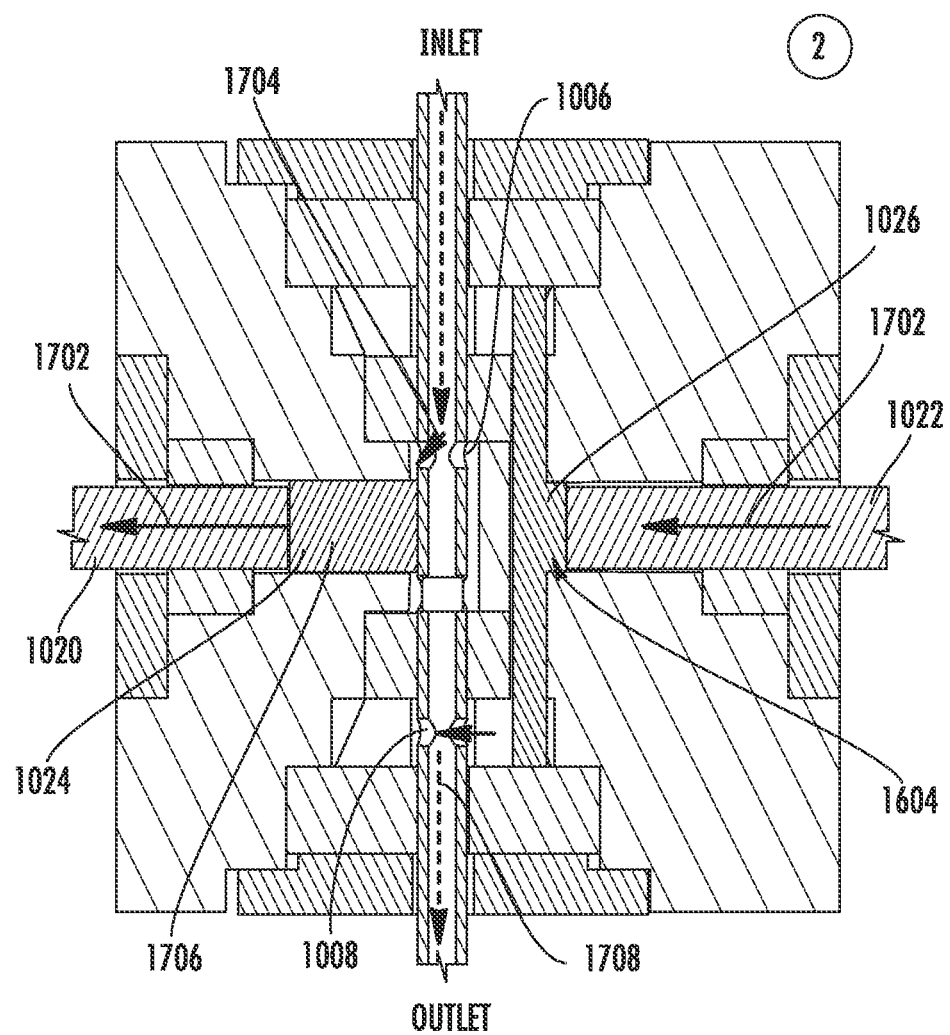

FIG. 17 illustrates a second stage of operation of the valve system 1000 (subsequent to the stage of operation of the valve system 1000 as shown in FIG. 16). As shown in FIG. 17, the pistons 1020 and 1022 are both operable to be actuated (e.g., in unison) to move in a direction 1702. As shown by flow indicators 1704, fluid 1706 may be draw in from the inlet component 1012 to the pump chamber 1024. Further, as shown by flow indicators 1708, the stored fluid 1604 (e.g., the same fluid as the fluid 1706 but referenced separately to distinguish locations of the fluids) may be pushed or pumped out through the outlet component 1014. The radial seals of the septa 1016 and 1018 (as described herein) may provide sealing against the pumping pressures along with the fluidic channels positioned between the tube 1004 and the pump chambers 1024 and 1026.

Figure 18:
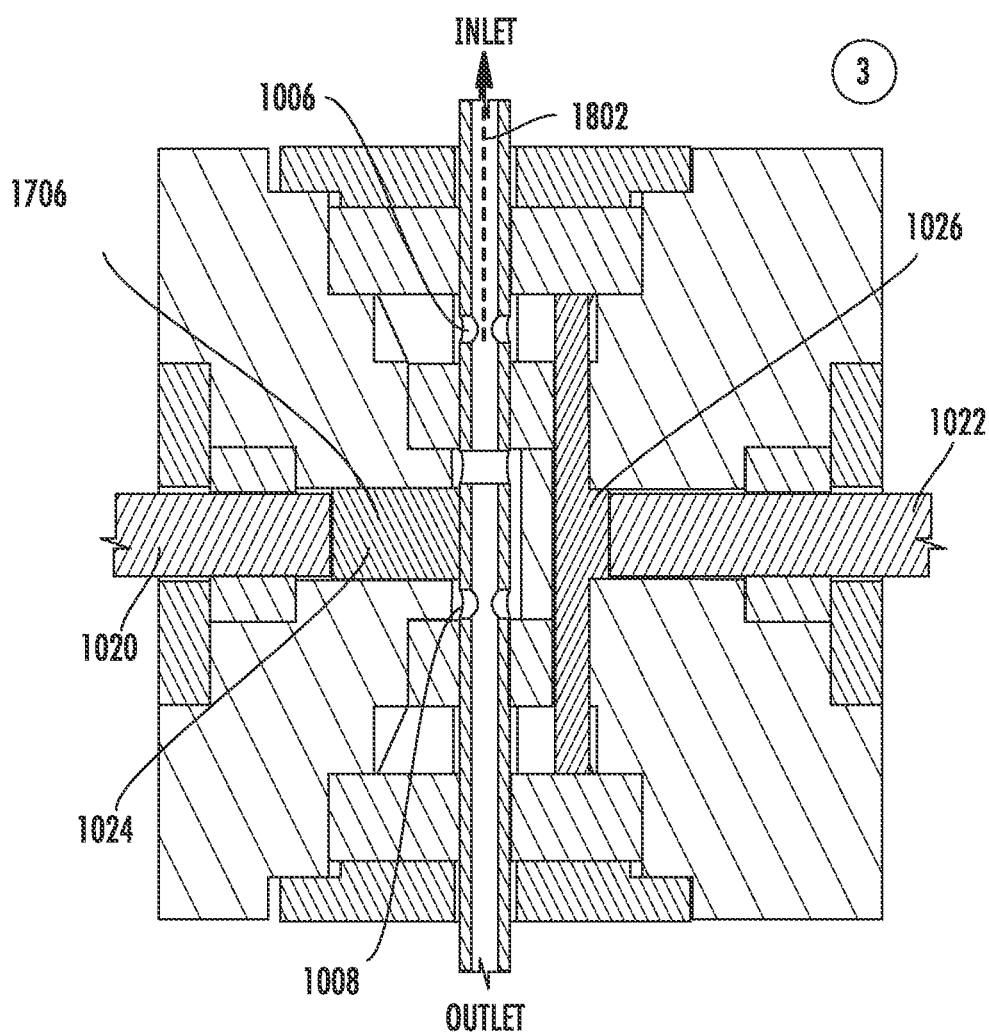

FIG. 18 illustrates a third stage of operation of the valve system 1000 (subsequent to the stage of operation of the valve system 1000 as shown in FIG. 17). As shown in FIG. 18, the tube 1004 is actuated to move in a direction 1802. Specifically, the tube 1004 is moved to position the side port 1006 (i.e., the side port connected to the inlet component 1012) to be coupled to the piston 1022/piston chamber 1026. Further, the side port 1008 (i.e., the side port coupled to the outlet component 1014) is positioned to be coupled the first piston 1020/piston chamber 1024. Further, as shown in FIG. 18, the fluid 1706 drawn in during the prior operational step is positioned within the pump chamber 1024. The pump chamber 1026 may be devoid of any, or substantially any, fluid.

Figure 19:
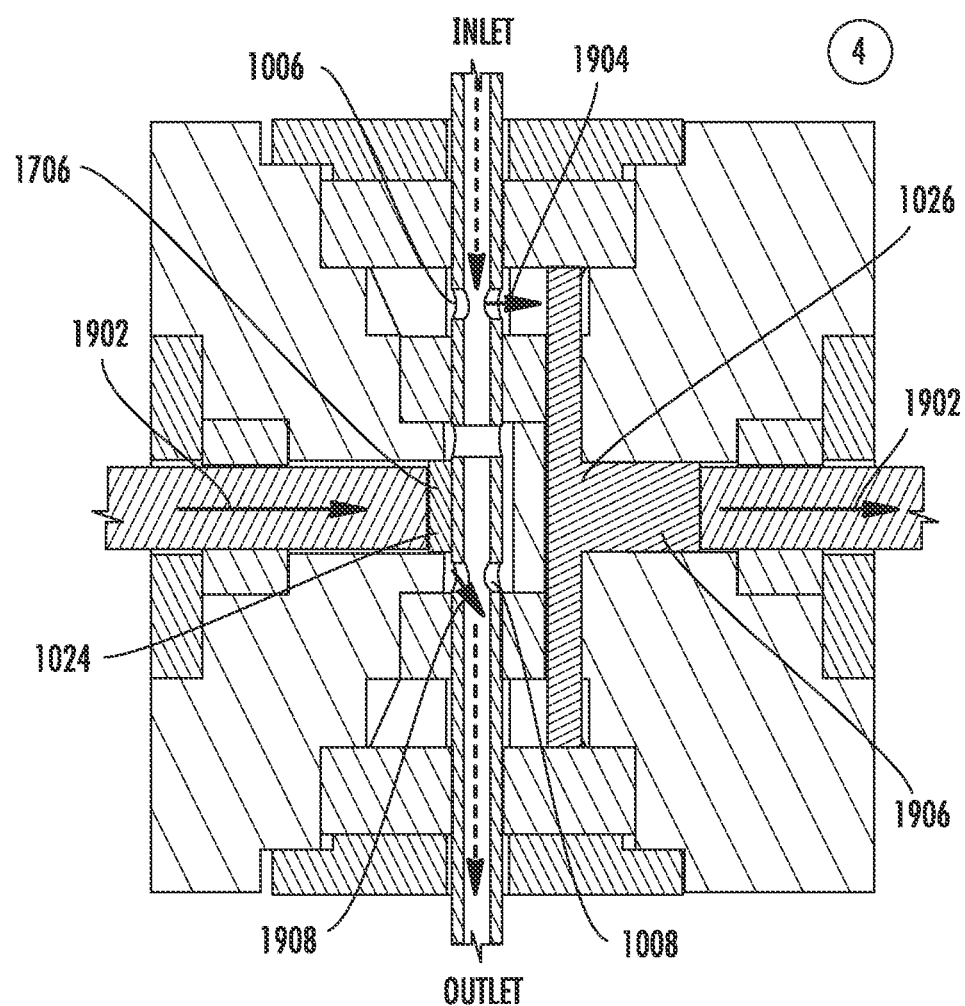

FIG. 19 illustrates a fourth stage of operation of the valve system 1000 (subsequent to the stage of operation of the valve system 1000 as shown in FIG. 18). As shown in FIG. 19, the pistons 1020 and 1022 are both actuated (e.g., in unison) to move in a direction 1902. As shown by flow indicators 1904, fluid 1906 may be draw in from the inlet component 1012 to the pump chamber 1026. Further, as shown by flow indicators 1908, the stored fluid 1706 (e.g., the same fluid as the fluid 1906 but referenced separately to distinguish locations of the fluids) may be pushed or pumped out through the outlet component 1014.

The valve system 1000 may repeat the steps illustrated in FIGS. 16-19 to implement a subsequent cycle of drawing in the fluid into the valve system 1000 from the reservoir and pushing it out for delivery to a patient.

Each example described herein may be part of a drug delivery system including, for example, a wearable drug delivery system.

Certain examples of the present invention were described above. It is, however, expressly noted that the present invention is not limited to those examples, but rather the intention is that additions and modifications to what was expressly described herein are also included within the scope of the invention. Moreover, it is to be understood that the features of the various examples described herein were not mutually exclusive and may exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A valve system, comprising:
a valve body;
a first septum positioned within the valve body;
a second septum positioned within the valve body and aligned with the first septum along a first axis;
a first piston coupled to a first pump chamber and positioned on a first side of the first septum and a first side of the second septum;
a second piston coupled to a second pump chamber and positioned on a second side of the first septum and a second side of the second septum, wherein the first piston and the second piston are aligned along a second axis perpendicular to the first axis; and
a tube piercing through the first septum and the second septum, the tube comprising a first side port, a second side port, and a center plug positioned between the first and second side ports.

2. The valve system of claim 1, wherein the tube is positioned through the valve body and the first septum and the second septum and positioned between the first and second pistons.

3. The valve system of claim 1, wherein the first side port is coupled to an inlet component portion of the tube and the second side port coupled to an outlet component portion of the tube.

4. The valve system of claim 3, wherein the inlet component portion is coupled to a reservoir storing a fluid and the outlet component portion coupled to a fluid path component.

5. The valve system of claim 1, wherein during a first stage of operation, the tube is operable to be moved to couple the first side port to the first piston and the first pump chamber and to couple the second side port to the second piston and the second pump chamber.

6. The valve system of claim 5, wherein during a second stage of operation subsequent to the first stage of operation, the first and second pistons are both operable to be moved in a first direction to draw fluid into the first pump chamber through an inlet component portion and the first side port and to pump out fluid from the second pump chamber through the second side port and an outlet component portion.

7. The valve system of claim 6, wherein during a third stage of operation subsequent to the second stage of operation, the tube is operable to be moved to couple the first side port to the second piston and the second pump chamber and to couple the second side port to the first piston and the first pump chamber.

8. The valve system of claim 7, wherein during a fourth stage of operation subsequent to the third stage of operation, the first and second pistons are both operable to be moved in a second direction opposite the first direction to draw fluid into the second pump chamber through the inlet component portion and the first side port and to pump out fluid from the first pump chamber through the second side port and the outlet component portion.

9. The valve system of claim 1, wherein the first septum includes a first angled opening, wherein the first angled opening is configured to allow a bidirectional flow of fluid.

10. The valve system of claim 9, wherein the first septum includes a second angled opening, wherein the second angled opening is configured to allow a bidirectional flow of fluid.

11. A drug delivery device, comprising:
   a valve body;
   a first septum positioned within the valve body;
   a second septum positioned with the valve body and aligned with the first septum, wherein the first septum forms a first radial seal facing the valve body and the second septum forms a second radial seal facing the valve body;
   a first piston coupled to a first pump chamber and positioned on a first side of the first septum and a first side of the second septum;
   a second piston coupled to a second pump chamber and positioned on a second side of the first septum and a second side of the second septum; and
   a tube piercing through the first septum and the second septum, the tube comprising a first side port, a second side port, and a center plug positioned between the first and second side ports.

* * * * *